US011350833B2

(12) United States Patent
Aelen (10) Patent No.: US 11,350,833 B2
(45) Date of Patent: Jun. 7, 2022

(54) DEVICE COMPRISING A BLOOD PRESSURE SENSOR AND A METHOD FOR CONTROLLING THE DEVICE

(71) Applicant: KONINKLIJKE PHILIPS N.V., Eindhoven (NL)

(72) Inventor: Paul Aelen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 265 days.

(21) Appl. No.: 16/345,505

(22) PCT Filed: Nov. 1, 2017

(86) PCT No.: PCT/EP2017/077944
§ 371 (c)(1),
(2) Date: Apr. 26, 2019

(87) PCT Pub. No.: WO2018/083108
PCT Pub. Date: May 11, 2018

(65) Prior Publication Data
US 2019/0307339 A1 Oct. 10, 2019

(30) Foreign Application Priority Data
Nov. 7, 2016 (EP) .................................. 16197456

(51) Int. Cl.
*A61B 5/022* (2006.01)
*A61B 5/00* (2006.01)
*A61B 5/11* (2006.01)

(52) U.S. Cl.
CPC ........ *A61B 5/02225* (2013.01); *A61B 5/0077* (2013.01); *A61B 5/1121* (2013.01);
(Continued)

(58) Field of Classification Search
CPC ... A61B 5/021; A61B 5/02225; A61B 5/0077; A61B 5/0079; A61B 5/1121;
(Continued)

(56) References Cited

U.S. PATENT DOCUMENTS 6,893,402 B2 * 5/2005 Freund .................. A61B 5/022
600/485
6,940,545 B1 * 9/2005 Ray ..................... G06K 9/00228
348/222.1
(Continued)

FOREIGN PATENT DOCUMENTS

JP  10216094  8/1998
JP  2007054648  3/2007
(Continued)

OTHER PUBLICATIONS

International Search Report and Written Opinion, International Application No. PCT/EP2017/077944, dated Feb. 1, 2018.
(Continued)

*Primary Examiner* — Rene T Towa (57) ABSTRACT

There is provided a device comprising a blood pressure sensor for sensing blood pressure and a method for controlling the device. An angle of the device with respect to the direction of gravity is determined (202) and a location of one or more features of the user holding the device is identified (204). A height of the blood pressure sensor relative to a heart level of the user is determined based on the determined angle of the device with respect to the direction of gravity and the identified location of the one or more features of the user (206). The device is controlled based on the determined height of the blood pressure sensor relative to the heart level of the user (208).

20 Claims, 3 Drawing Sheets

(52) U.S. Cl.
CPC .......... *A61B 5/1128* (2013.01); *A61B 5/4887* (2013.01); *A61B 5/6844* (2013.01); *A61B 5/6898* (2013.01); *A61B 5/70* (2013.01); *A61B 5/7221* (2013.01); *A61B 5/742* (2013.01); *A61B 5/7475* (2013.01); *A61B 5/1126* (2013.01); *A61B 5/681* (2013.01); *A61B 2560/0261* (2013.01); *A61B 2562/0219* (2013.01); *A61B 2562/0247* (2013.01); *A61B 2562/0252* (2013.01); *A61B 2562/0261* (2013.01)

(58) Field of Classification Search
CPC ....... A61B 5/1128; A61B 5/6844; A61B 5/70; A61B 5/7221; A61B 5/7475; A61B 5/1126; A61B 5/681; A61B 2560/0261; A61B 2562/0219; A61B 2562/024; A61B 2562/0252; A61B 5/6898; A61B 5/6801; A61B 5/4887; A61B 5/742; A61B 5/7425; A61B 5/743; A61B 2562/0261; A61G 5/6802
See application file for complete search history.

(56) References Cited

U.S. PATENT DOCUMENTS

| | | | |
|---|---|---|---|
| 10,786,161 B1 * | 9/2020 | Archdeacon | A61B 5/7278 |
| 2007/0276266 A1 | 11/2007 | Baba | |
| 2010/0049059 A1 | 2/2010 | Ha et al. | |
| 2012/0190944 A1 | 7/2012 | Thaveeprungsriporn et al. | |
| 2013/0237865 A1 * | 9/2013 | Sato | A61B 5/1072 600/499 |
| 2015/0366456 A1 * | 12/2015 | Takamori | A61B 5/0077 600/480 |
| 2017/0332963 A1 * | 11/2017 | Murakami | A61B 5/681 |

FOREIGN PATENT DOCUMENTS

| | | | | |
|---|---|---|---|---|
| JP | 3140916 U | * | 4/2008 | ............ A61B 5/022 |
| WO | 2013001265 A2 | | 1/2013 | |
| WO | 2014125431 A1 | | 8/2014 | |
| WO | WO-2014155750 A1 | * | 10/2014 | ........... G06T 7/0016 |
| WO | 2016096919 A1 | | 6/2016 | |

OTHER PUBLICATIONS

Geddes L.A., Handbook of Blood Pressure Measurement, ISBN 978-1468471724, 1991.
Hattersley, L., "How does Force Touch work?", https://www.macworld.co.uk/feature/mac/how-does-force-touch-work-3606551/, Accessed Apr. 2019.
Benajmin, J., "Using the iPhone 6s 3D Touch display to weigh items [Video]", Oct. 24, 2015, https://www.downloadblog.com/2015/10/24/using-the-iphone-6s-3d-touch-display-to-weigh-items-video/.
X. F. Teng and Y. T. Zhang, "The effect of contacting force on photoplethysmographic signals," Physiol. Meas. Physiol. Meas, vol. 25, No. 25, pp. 1323-1335, 2004.
X. F. Teng and Y. T. Zhang, "The effect of applied sensor contact force on pulse transit time.," Physiol. Meas., vol. 27, pp. 675-684, 2006.
X.-F. Teng and Y.-T. Zhang, "Theoretical study on the effect of sensor contact force on pulse transit time.," IEEE Trans. Biomed. Eng., vol. 54, No. 8, pp. 1490-1498, 2007.
K. Matsumura, P. Rolfe, J. Lee, and T. Yamakoshi, "iPhone 4s photoplethysmography: Which light color yields the most accurate heart rate and normalized pulse volume using the iPhysioMeter application in the presence of motion artifact?," PLoS One, vol. 9, No. 3, pp. 1-12, 2014.
"PPG photoplethysmography at fingertips with a smartphone", YouTube video, Published Aug. 18, 2015, https://www.youtube.com/watch?v=tSsZrrvGsol&spfreload=5.
Ilango, S. et al., "A Non-Invasive Blood Pressure Measurement using Android Smart Phones", Journal of Dental and Medical Sciences, vol. 13, Issue 1 Ver. IV (Jan. 2014), pp. 28-31.

* cited by examiner

DEVICE COMPRISING A BLOOD PRESSURE SENSOR AND A METHOD FOR CONTROLLING THE DEVICE

CROSS-REFERENCE TO PRIOR APPLICATIONS

This application is the U.S. National Phase application under 35 U.S.C. § 371 of International Application No. PCT/EP2017/077944, filed on 1 Nov. 2017, which claims the benefit of European Patent Application No. 16197456.3, filed on 7 Nov. 2016. These applications are hereby incorporated by reference herein.

TECHNICAL FIELD OF THE INVENTION

The invention relates to a device comprising a blood pressure sensor and a method for controlling the device.

BACKGROUND TO THE INVENTION

Blood pressure (BP), or more precisely, arterial blood pressure, is the pressure exerted by circulating blood on arterial vessel walls. It is one of the key vital signs to establish the well-being of a subject. Since blood pressure is dynamic and changes periodically due the pumping action of the heart, blood pressure is typically described by systolic blood pressure (SBP), which is the maximal blood pressure during the heart cycle, diastolic blood pressure (DBP), which is the minimal blood pressure during the heart cycle, and mean arterial blood pressure (MAP), which is the average blood pressure during the heart cycle.

In the past, non-invasive blood pressure measurements were typically performed by using a sphygmomanometer, which uses a column of mercury to reflect blood pressure. Nowadays, devices for blood pressure measurements are often cuff-based. The measurement procedure is often automated, especially when the device is not intended for the professional caregiver. The most commonly used and clinically accepted automatic blood pressure measurement uses the oscillometric blood pressure measurement principle. This measurement principle generally consists of placing a cuff around a limb (usually the upper arm) of a subject and inflating it rapidly. After this, cuff pressure is gradually or stepwise decreased, during which the arterial volume oscillations cause small pressure oscillations in the cuff. The diastolic blood pressure (DBP) and the systolic blood pressure (SBP) are estimated from these cuff pressure dependent amplitudes of the cuff pressure or volume oscillations using heuristic algorithms. The mean arterial pressure (MAP) is then usually calculated from the diastolic blood pressure (DBP) and the systolic blood pressure (SBP) using a heuristic formula or by assuming it is equal to the pressure at maximum oscillations. Instead of using the pressure oscillations during deflation, the oscillations can also be measured during inflation.

Other blood pressure measurement techniques have been developed that do not require an external cuff. This has been possible due to the rapid developments in the mobile device industry (particularly, the smartphone industry), which allow a user to have a plurality of high quality sensors in a single device. For example, a user of a smartphone is now able to perform an oscillometric blood pressure measurement using sensors in a smartphone. WO 2016/096919 A1 discloses an example of a personal hand-held monitor for the measurement of a subject's blood pressure, where a pressure sensor is embedded in the monitor to provide an electrical signal indicative of the pressure applied to it by a body part of the subject such that the flow of blood in the body part can be detected and a blood pressure measurement provided.

However, while these recent techniques that eliminate the need for a cuff are more convenient for the user, the blood pressure measurements acquired by these techniques can suffer from inaccuracies due to the effects of hydrostatic pressure. In order to avoid the effects of hydrostatic pressure, blood pressure measurements need to be taken at or close to the level of the heart of the user since any height difference between the blood pressure measurement location and the heart level will result in a hydrostatic offset. If the blood pressure measurements are taken above the level of the heart, the measurement results will be too low, whereas if the blood pressure measurements are taken below the level of the heart, the measurement results will be too high. For every centimetre difference between the blood pressure measurement location and the heart level, 0.73 mmHg is erroneously introduced to the blood pressure measurement. Thus, if the blood pressure measurement is taken from a finger while the arm is in a relaxed (i.e. in a hanging position), a height difference of 50 cm can easily be made, which can result in hydrostatic offsets of approximately 37 mmHg.

As an untrained user usually takes the blood pressure measurement in the home environment, it is often the case that the blood pressure measurements are taken at heights that are significantly different to the heart level of the user, which can introduce large errors in the blood pressure measurements. This is especially relevant for cuff-less devices, as cuff-less devices do not restrict the counter pressure to be applied at heart level, whereas cuff-based measurements on an upper arm will always be relatively close to the heart level. Therefore, a device aimed at minimising, preventing or eliminating hydrostatic effects to provide more accurate blood pressure measurements is required.

There is thus a need for an improved device comprising a blood pressure sensor and an improved method for controlling the device.

SUMMARY OF THE INVENTION

As noted above, the limitation with existing approaches is that errors can be introduced into blood pressure measurements due to hydrostatic effects. It would thus be valuable to have a device comprising a blood pressure sensor and a method for controlling the device in a manner that overcomes these existing problems.

Therefore, according to a first aspect of the invention, there is provided a method for controlling a device comprising a blood pressure sensor for sensing blood pressure. The method comprises determining an angle of the device with respect to the direction of gravity, identifying a location of one or more features of the user holding the device, determining a height of the blood pressure sensor relative to a heart level of the user based on the determined angle of the device with respect to the direction of gravity and the identified location of the one or more features of the user, and controlling the device based on the determined height of the blood pressure sensor relative to the heart level of the user.

In some embodiments, the one or more features of the user holding the device may comprise one or more anatomical features of the user holding the device. In some embodiments, the location of the one or more features may be identified in a displayed image of the user. In some embodiments, the location of the one or more features may be identified relative to a displayed predefined location range. In these embodiments, the height of the blood pressure sensor relative to a heart level of the user may be determined based on the determined angle of the device with respect to the direction of gravity and the identified location of the one or more features of the user in the image relative to the predefined location range.

In some embodiments, the height of the blood pressure sensor may be determined to be different to the heart level of the user where the determined angle of the device with respect to the direction of gravity is outside a predefined angle range and/or the identified location of the one or more features of the user is outside a predefined location range.

In some embodiments, the height of the blood pressure sensor may be determined to be at the heart level of the user where the determined angle of the device with respect to the direction of gravity is within a predefined angle range and/or the identified location of the one or more features of the user is within a predefined location range.

In some embodiments, controlling the device based on the determined height of the blood pressure sensor may comprise controlling the device to output to the user one or more of the determined angle of the device with respect to the direction of gravity and the identified location of the one or more features of the user when the height of the blood pressure sensor is determined to be different to the heart level of the user.

In some embodiments, controlling the device based on the determined height of the blood pressure sensor may comprise controlling the device to output to the user an instruction to adjust one or more of the angle of the device with respect to the direction of gravity and the location of the one or more features of the user when the height of the blood pressure sensor is determined to be different to the heart level of the user.

In some embodiments, controlling the device based on the determined height of the blood pressure sensor may comprise controlling the device to output to the user an error notification when the height of the blood pressure sensor is determined to be different to the heart level of the user.

In some embodiments, controlling the device based on the determined height of the blood pressure sensor may comprise controlling the blood pressure sensor to acquire a blood pressure measurement from the user when the height of the blood pressure sensor is determined to be at the heart level of the user.

In some embodiments, controlling the device based on the determined height of the blood pressure sensor may comprise controlling the blood pressure sensor to acquire a blood pressure measurement from the user when the height of the blood pressure sensor is determined to be different to the heart level of the user, and adjusting the acquired blood pressure measurement based on the difference between the height of the blood pressure sensor and the heart level of the user.

In some embodiments, the one or more features of the user may comprise any one or more of one or both eyes of the user, the mouth of the user, the nose of the user, and the facial outline of the user.

According to a second aspect of the invention, there is provided a computer program product comprising a computer readable medium, the computer readable medium having computer readable code embodied therein, the computer readable code being configured such that, on execution by a suitable computer or processor, the computer or processor is caused to perform the method or the methods described above.

According to a third aspect of the invention, there is provided a device comprising a blood pressure sensor for acquiring a blood pressure measurement from a user holding the device and a control unit. The control unit is configured to determine an angle of the device with respect to the direction of gravity, identify a location of one or more features of the user holding the device, determine a height of the blood pressure sensor relative to a heart level of the user based on the determined angle of the device with respect to the direction of gravity and the identified location of the one or more features of the user, and control the device based on the determined height of the blood pressure sensor relative to the heart level of the user.

In some embodiments, the one or more features of the user holding the device may comprise one or more anatomical features of the user holding the device. In some embodiments, the location of the one or more features may be identified in a displayed image of the user. In some embodiments, the location of the one or more features may be identified relative to a displayed predefined location range. In these embodiments, the height of the blood pressure sensor relative to a heart level of the user may be determined based on the determined angle of the device with respect to the direction of gravity and the identified location of the one or more features of the user in the image relative to the predefined location range.

In some embodiments, the device may further comprise an angular sensor and the control unit may be configured to control the angular sensor to determine the angle of the device with respect to the direction of gravity.

In some embodiments, the device may further comprise a camera and the control unit may be configured to control the camera to identify the location of the one or more features of the user when the user is, at least partially, in the field of view of the camera.

In some embodiments, the device may further comprise a user interface and, when the height of the blood pressure sensor is determined to be different to the heart level of the user, the control unit may be configured to control the user interface to output to the user any one or more of the determined angle of the device with respect to the direction of gravity, the identified location of the one or more features of the user, an instruction to adjust any one or more of the angle of the device with respect to the direction of gravity, the location of the one or more features of the user, and an angle of the body of the user, and an error notification.

In some embodiments, the blood pressure sensor may comprise any one or more of a volume sensor and a pressure sensor.

According to the aspects and embodiments described above, the limitations of existing techniques are addressed. In particular, according to the above-described aspects and embodiments, hydrostatic effects in blood pressure measurements can be prevented, reduced, or eliminated. In this way, more accurate blood pressure measurements can be acquired by way of a simple yet effective method.

There is thus provided an improved device comprising a blood pressure sensor and an improved method for controlling the device, which overcomes the existing problems.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, the invention provides an improved device comprising a blood pressure sensor and an improved method for controlling the device, which overcomes the existing problems.

Figure 1:
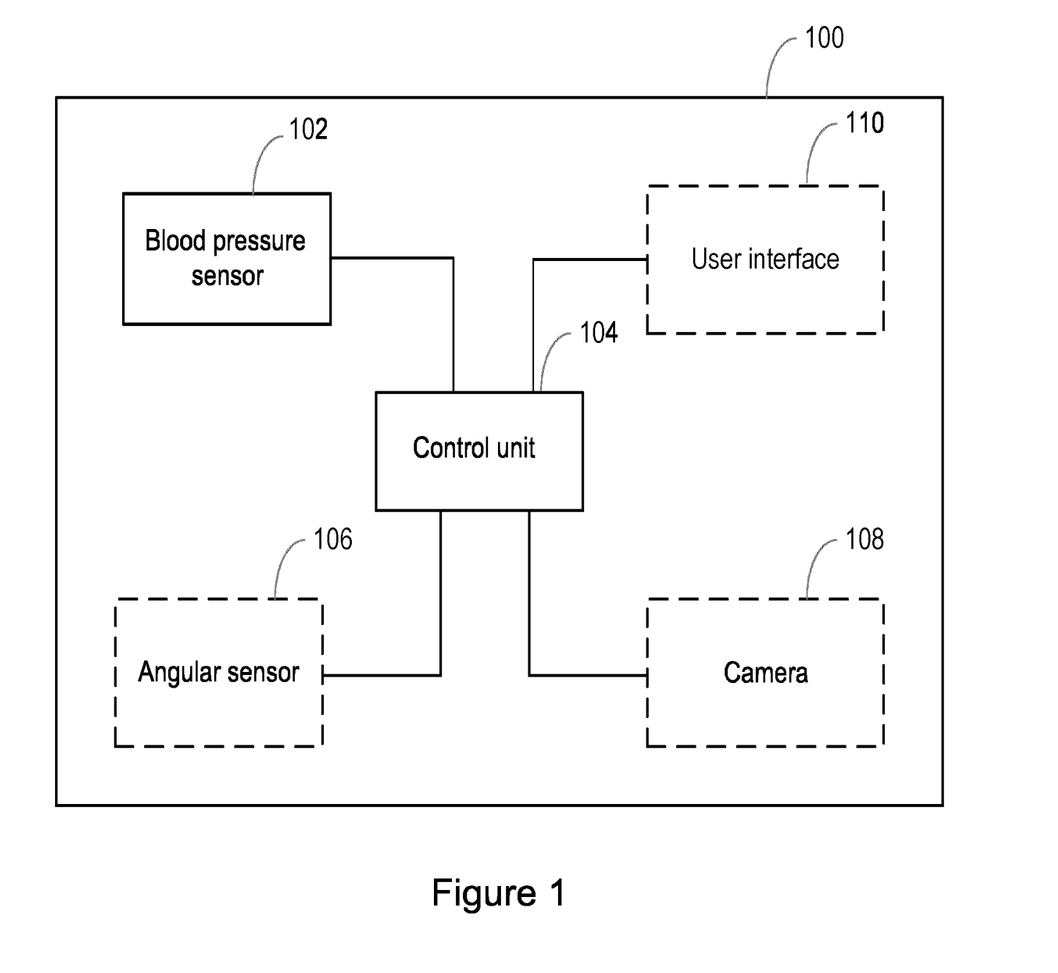
FIG. 1 is a block diagram of a device according to an embodiment.

FIG. 1 shows a block diagram of a device 100 according to an embodiment. In some embodiments, the device 100 may be a device dedicated for blood pressure measurements. In other words, the device 100 can be a blood pressure measurement device. Alternatively, in some embodiments, in addition to blood pressure measurements, the device 100 may also be intended for other purposes or uses. The device 100 may be a mobile device. For example, the device 100 can be a smart phone, a tablet, a smart watch, or any other mobile device.

As illustrated in FIG. 1, the device 100 comprises a blood pressure sensor 102 for sensing blood pressure (or for acquiring a blood pressure measurement) from a user holding the device 100. In operation, to acquire a blood pressure measurement, the user holds the device 100 (for example, in front of them) such that a part of the body of the user (for example, a finger or thumb of the user) is positioned at or contacts with the blood pressure sensor 102. The part of the body of the user may be in direct contact with the blood pressure sensor 102 or indirect contact with the blood pressure sensor 102.

In some embodiments, the user may be instructed (such as via a user interface of the device 100) to increase the pressure applied by the part of the body that is in contact with the blood pressure sensor 102. For example, the user may be instructed to increase the pressure applied by the part of the body that is in contact with the blood pressure sensor 102 by a pressure profile generated over time, which the user can follow by increasing the applied pressure. Examples of a pressure profile include, but are not limited to, a numerical target that increases over time, a line or bar that becomes increasingly full as pressure is increased with target pressures at one or more points in time, or any other pressure profile.

The blood pressure sensor 102 of the device 100 can comprise any sensor, or any combination or sensors, suitable to acquire a blood pressure measurement from a user holding the device 100. The blood pressure measurement may, for example, be acquired from arterial oscillations detected by the blood pressure sensor 102. An increase in pressure applied by the part of the body of the user that is in contact with the blood pressure sensor 102 can result in arterial oscillations, which can then be detected by the blood pressure sensor 102. The blood pressure sensor 102 can comprise any one or more of a volume sensor, a pressure sensor, or any other sensor, or any combination of sensors, suitable to acquire a blood pressure measurement from a user holding the device 100.

A volume sensor can comprise any volume sensor that is suitable to detect arterial oscillations (specifically, volumetric oscillations) from the part of the body of the user that is positioned at the volume sensor of the device 100, which can be used to acquire a blood pressure measurement. Examples of a volume sensor include, but are not limited to, a light sensor, or any other volume sensor, or any combination of volume sensors. A light sensor can comprise any light sensor that is suitable to detect light indicative of volumetric oscillations from a user holding the device 100, which can be used to acquire a blood pressure measurement. For example, a light sensor can comprise an image sensor, a plethysmography (PG) sensor (such as a photoplethysmography (PPG) sensor), or any other light sensor, or any combination of light sensors.

An image sensor can comprise any image sensor that is suitable to acquire an image from a user holding the device 100, which can be used to acquire a blood pressure measurement. Examples of an image sensor include, but are not limited to, a camera, a video recording device, or any other image sensor, or any combination of image sensors. The image may comprise a single image frame or a plurality of image frames. For example, the plurality of image frames may be in the form of a "live", instantaneous, or real-time (or near real-time) series of image frames or video of the user holding the device. The image acquired by the image sensor can be indicative of arterial oscillations (specifically, volumetric oscillations) in the part of the body of the user that is in the image. In some embodiments, for example, the image acquired by the image sensor may be averaged to acquire a volume measurement.

A photoplethysmography (PPG) sensor can comprise any photoplethysmography sensor suitable to acquire photoplethysmographic data from the user holding the device 100, which can be used to acquire a blood pressure measurement. Examples of a photoplethysmography sensor include, but are not limited to, a reflective PPG sensor, a transmissive PPG sensor, or any other photoplethysmography sensor, or any combination of photoplethysmography sensors. The photoplethysmographic data acquired by the photoplethysmography sensor can be indicative of arterial oscillations (specifically, volumetric oscillations) in the part of the body of the user that is positioned at the photoplethysmography sensor of the device 100.

In some embodiments, a light sensor (such as a PPG sensor) can comprise a light source (for example, a white light emitting diode LED, a single wavelength light such as a light emitting in the red region, or any other light source) and an associated light detector. For example, in some embodiments, a light source may be operable to project light onto a part of the body of the user holding the device 100 and the light detector may be operable to detect transmitted or reflected light. The light detected by the light detector can be indicative of arterial oscillations (specifically, volumetric oscillations) in the part of the body of the user onto which light is projected.

A pressure sensor can comprise any pressure sensor that is suitable to acquire the applied pressure and the arterial oscillations (specifically, pressure oscillations) from a part of the body of the user that is in direct or indirect contact with the pressure sensor of the device 100, which can be used to acquire a blood pressure measurement. Examples of a pressure sensor include, but are not limited to, a pressure sensitive display, a pressure sensitive element below a display (such as a foil, thin-film flexible printed circuit, or similar), a force sensor where a contact area of the force sensor with a part of the body of the user is known (for example, assumed to be constant) or can be measured, or any other pressure sensor, or any combination of pressure sensors. The pressure oscillations can be determined from the force detected by a force sensor where the contact area is known or measured since pressure is equal to the force per unit area. In some embodiments, a pressure sensor can comprise multiple force sensors integrated over an area.

A force sensor can comprise any force sensor suitable to detect a force applied by the user holding the device 100, which can be used to acquire a blood pressure measurement. Examples of a force sensor include, but are not limited to, a force sensitive display, a force sensitive element below a display (such as a foil, thin-film flexible printed circuit, or similar), a strain gauge, a load cell (for example, a structure comprising multiple strain gauges, or any other force sensor, or any combination of force sensors.

Although examples have been provided for the blood pressure sensor 102, it will be understood that any other blood pressure sensor, or any combination of blood pressure sensors, suitable to acquire a blood pressure measurement from the user can be used.

As illustrated in FIG. 1, the device 100 also comprises a control unit 104. The control unit 104 controls the operation of the device 100 and can implement the method describe herein. The control unit 104 can comprise one or more processors, processing units, multi-core processors or modules that are configured or programmed to control the device 100 in the manner described herein. In particular implementations, the control unit 104 can comprise a plurality of software and/or hardware modules that are each configured to perform, or are for performing, individual or multiple steps of the method according to embodiments of the invention.

Briefly, the control unit 104 is configured to determine an angle of the device with respect to the direction of gravity, identify a location of one or more features of the user holding the device, determine a height of the blood pressure sensor relative to a heart level of the user based on the determined angle of the device with respect to the direction of gravity and the identified location of the one or more features of the user, and control the device based on the determined height of the blood pressure sensor relative to the heart level of the user.

In some embodiments, as illustrated in FIG. 1, the device 100 can further comprise an angular sensor 106. Examples of an angular sensor include, but are not limited to, an accelerometer or gravitational sensor (such as a single-axis accelerometer, a dual-axis accelerometer, or a three-axis accelerometer), a gyroscope, a tilt-sensor, or any other angular sensor, or any combination of angular sensors. The angular sensor 106 can be for use in determining the angle of the device with respect to the direction of gravity. For example, in embodiments where the device 100 comprises an angular sensor 106, the control unit 104 can be configured to control the angular sensor 106 to determine the angle of the device with respect to the direction of gravity.

In some embodiments, as illustrated in FIG. 1, the device 100 can further comprise a camera 108. The camera 108 can be for use in identifying the location of the one or more features of the user when the user is, at least partially, in the field of view of the camera 108. For example, the control unit 104 can be configured to control the camera 108 to identify the location of the one or more features of the user when the user is, at least partially, in the field of view of the camera 108. The camera 108 can be any camera that is directed at the user. Thus, alternatively or in addition to the device comprising a camera 108, a camera 108 may be external to (i.e. separate to or remote from) the device 100.

In some embodiments, as illustrated in FIG. 1, the device 100 can further comprise a user interface 110. Alternatively or in addition, a user interface 110 may be external to (i.e. separate to or remote from) the device 100. A user interface 100 can be for use in providing a user of the device 100 with information, data, signals, or measurements resulting from the method according to the invention. For example, the control unit 104 can be configured to control a user interface 110 to provide (for example, render, output, or display) information, data, signals, or measurements resulting from the method to the user of the device 100.

In some embodiments, the control unit 104 may be configured to control a user interface 110 to display an image of the user. As mentioned earlier, the image may comprise a single image frame or a plurality of image frames. For example, the control unit 104 may be configured to control the user interface 110 to display a "live", instantaneous, or real-time (or near real-time) series of image frames or video of the user holding the device 100. The control unit 104 may also be configured to control the user interface 110 to display a predefined location range for the one or more features of the user. For example, the predefined location range may be displayed over or through the image of the user. In some embodiments, the image of the user and the predefined location range may be displayed on the device 100 comprising the blood pressure sensor 102. Alternatively, in other embodiments, the image of the user and the predefined location range may be displayed on a device that is a different device to the device 100 that comprises the blood pressure sensor 102. For example, the device on which the image of the user and the predefined location range are displayed may be external to (i.e. separate to or remote from) the device 100 comprising the blood pressure sensor 102.

In some embodiments, for example, the control unit 104 can be configured to control a user interface 110 to provide (for example, render, output, or display) to the user one or more blood pressure measurements acquired by the blood pressure sensor 102 of the device 100. Alternatively or in addition, in some embodiments, when the control unit 104 of the device 100 determines that the height of the blood pressure sensor 102 is different to the heart level of the user, the control unit 104 can be configured to control a user interface 110 to provide (for example, render, output, or display) to the user any one or more of the determined angle of the device with respect to the direction of gravity, the identified location of the one or more features of the user, an instruction to adjust one or more of the angle of the device with respect to the direction of gravity and the location of the one or more features of the user, an error notification, or any other information resulting from the method described herein.

Alternatively or in addition, a user interface 110 may be configured to receive a user input. In other words, a user interface 110 may allow a user of the device 100 to manually enter instructions, data, or information. The control unit 104 may be configured to acquire a user input from the user interface 110.

A user interface 110 may be any user interface that enables rendering (or output or display) of information, data, signals, or measurements to a user of the device 100. Alternatively or in addition, a user interface 110 may be any user interface that enables a user of the device 100 to provide a user input, interact with and/or control the device 100. For example, a user interface 110 may comprise one or more switches, one or more buttons, a keypad, a keyboard, a touch screen or an application (for example, on a smartphone, tablet, or similar), a display screen, a graphical user interface GUI or any other visual rendering component, one or more speakers, one or more microphones or any other audio component, one or more lights, a component for providing tactile feedback (such as a vibration function), or any other user interface component, or combination of user interface components.

Although not illustrated in FIG. 1, in some embodiments, the device 100 may also comprise a memory configured to store program code that can be executed by the control unit 104 to perform the method described herein. The memory can be used to store information, data, signals and measurements acquired or made by the control unit 104 of the device 100. For example, the memory may be used to store blood pressure measurements acquired by the blood pressure sensor 102 from the user of the device 100.

Although not illustrated in FIG. 1, in some embodiments, the device 100 may also comprise a communications interface for enabling the device 100 to communicate with any sensors, interfaces, units, memories, devices or any other components that are internal or external to the device 100. The communications interface may communicate with any sensors, interfaces, units, memories, devices or any other components wirelessly or via a wired connection. For example, in an embodiment where the camera 108 is external to the device 100, the communications interface may communicate with the external camera 108 wirelessly or via a wired connection. Similarly, in an embodiment where a user interface 110 is external to the device 100, the communications interface may communicate with the external user interface wirelessly or via a wired connection.

Thus, it will be appreciated that FIG. 1 only shows the components required to illustrate this aspect of the invention, and in a practical implementation the device 100 may comprise additional components to those shown. For example, the device 100 may comprise a battery or other power supply for powering the device 100 or means for connecting the device 100 to a mains power supply.

Figure 2:
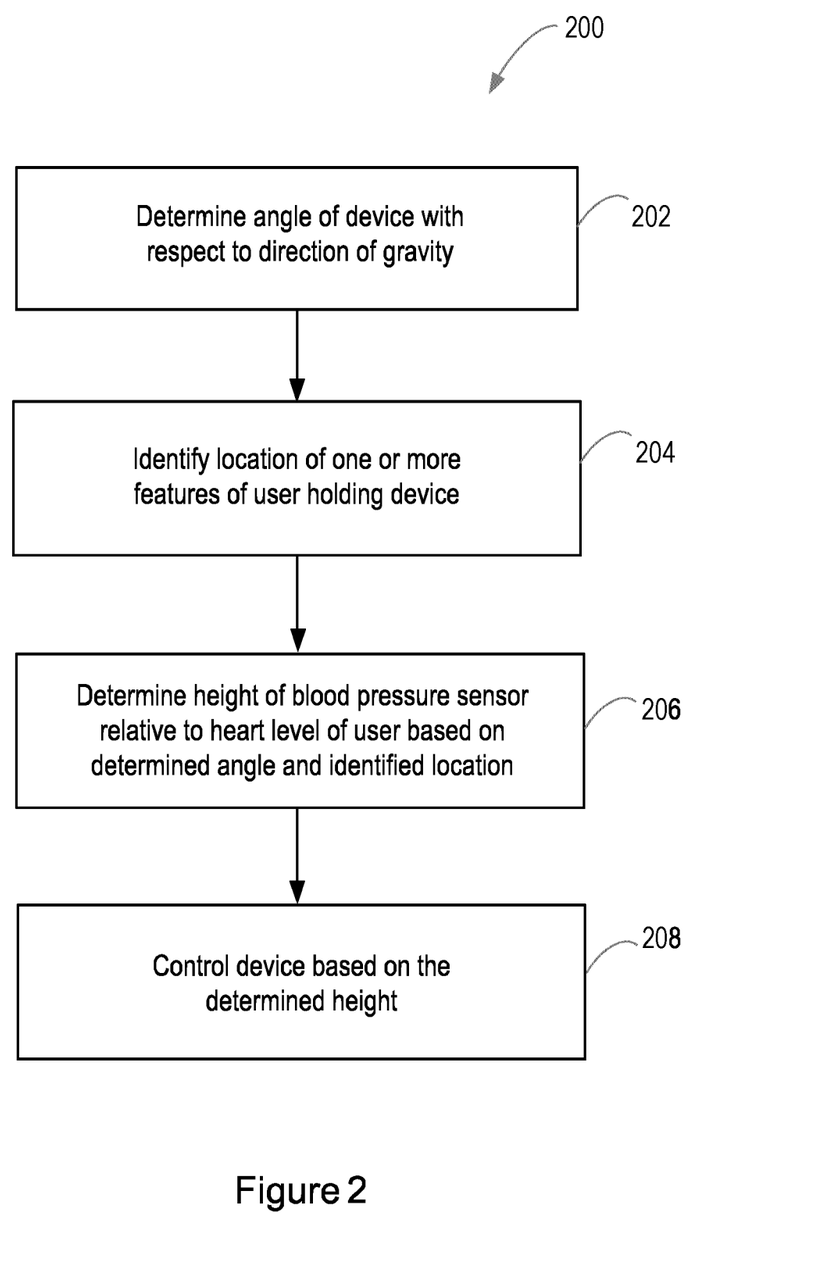
FIG. 2 is a flow chart illustrating a method according to an embodiment.

FIG. 2 illustrates a method 200 for controlling the device 100 comprising the blood pressure sensor 102. The illustrated method 200 can generally be performed by or under the control of the control unit 104 of the device 100.

As mentioned previously, in operation, the user holds the device 100 (for example, in front of them) such that a part of the body of the user (for example, a finger or thumb of the user) is positioned at or contacts with the blood pressure sensor 102. In some embodiments, although not illustrated, the position of the part of the body of the user on the device may be detected to ensure that the user is holding the device 100 correctly. For example, where the blood pressure sensor 102 comprises a camera and a display (such as a force or pressure sensitive display) of the device 100, the user may place a finger (such as an index finger) of a hand in front of the camera and a thumb of the hand on the display for the blood pressure measurement. The position of the thumb on the display can be measured and the camera can be used to detect the position of the finger to ensure that the user is holding the device 100 correctly. Alternatively or in addition, in some embodiments, the blood pressure sensor 102 may be located at one or more fixed points on the device 100, which can be indicated to the user. For the purpose of the method disclosed herein, it may be assumed that the device 100 is held approximately or exactly perpendicular to the body of the user.

With reference to FIG. 2, at block 202, an angle of the device 100 is determined with respect to the direction of gravity (or compared to the ground level or earth). For example, as mentioned earlier, the control unit 104 can be configured to control an angular sensor 106 of the device 100 to determine the angle of the device with respect to the direction of gravity. In some embodiments, the angle of the body of the user may be inferred from the angle of the device 100 with respect to the direction of gravity.

As an angular sensor can measure gravitational force, the gravitational force component on the angular sensor can be used to determine the angle of the device 100 with respect to gravity. As mentioned earlier, the angular sensor can comprise an accelerometer (such as a single-axis accelerometer, a dual-axis accelerometer, a three-axis accelerometer), a gyroscope, a tilt-sensor, or similar and thus the angle of the device 100 with respect to gravity can be determined in any of the standard ways in respect of these angular sensors. For example, as is known, the acceleration due to gravity can be measured and related back to the reference frame of the device 100 to determine the angle of the device 100 with respect to gravity.

At block 204, a location of one or more features (or landmarks) of the user holding the device 100 are identified. For example, as mentioned earlier, the control unit 104 can be configured to control a camera 108 of the device 100 to identify the location of the one or more features of the user when the user is (at least partially) in the field of view of the camera 108. The one or more features of the user can comprise one or more anatomical (e.g. physical) features of the user. In some embodiments, the one or more features of the user may comprise one or more features of the torso (or upper torso) of the user, such as one or more shoulders of the user, or any other features of the torso of the user, or any combination of features of the torso of the user. Alternatively or in addition, in some embodiments, the one or more features of the user may comprise the neck of the user. Alternatively or in addition, in some embodiments, the one or more features of the user may comprise one or more facial features of the user, for example, any one or more of the facial outline of the user, one or both eyes of the user, the nose of the user, the mouth of the user, or any other facial features of the user, or any combination of facial features of the user. Although examples have been provided for the one or more features of the user, the person skilled in the art will be aware of other features of the user, or any combination of features of the user, that may be used.

In some embodiments, the method may further comprise determining the distance of the device 100 with respect to the body based on the size, location, or both the size and location, of the one or more features. The distance may, for example, be determined as a horizontal distance. The distance can be indicative of the amount an arm of the user is stretched while holding the device 100 and can be used to improve the measurement of height of the device relative to the heart level. The distance may, for example, be determined based on the apparent size of the one or more features identified by the camera 108. For example, the larger a feature appears, the closer the feature is to the camera 108 (which can be indicative of a bent arm) and, similarly, the smaller a feature appears, the farther the feature is from the camera 108 (which can be indicative of a straight arm).

At block 206, a height of the blood pressure sensor 102 relative to a heart level of the user is determined based on the determined angle of the device 100 with respect to the direction of gravity and the identified location of the one or more features of the user.

In some embodiments, the method comprises determining whether the determined angle of the device 100 with respect to the direction of gravity is within (or outside) a predefined angle range. In other words, it may be determined whether the determined angle of the device 100 with respect to the direction of gravity is between (or falls outside) a minimum threshold value for the angle and a maximum threshold value for the angle. The predefined angle range (or minimum and maximum threshold values for the angle) can be set to indicate that the device 100 is held upright or substantially upright. In one example, the predefined angle range is between −30 degrees and +30 degrees. However, it will be understood that other predefined angles may be used instead. Similarly, in some embodiments, the method may further comprise determining whether the identified location of the one or more features of the user is within (or outside) a predefined location range. For example, the predefined location range may be a predefined location range on a display of the device 100 comprising the blood pressure sensor 102 or another device. The predefined location range on the display may be defined by one or more lines or shapes.

In these embodiments, the height of the blood pressure sensor 102 may be determined to be different to the heart level of the user where the determined angle of the device with respect to the direction of gravity is outside a predefined angle range, the identified location of the one or more features of the user is outside a predefined location range, or both the determined angle of the device with respect to the direction of gravity is outside a predefined angle range and the identified location of the one or more features of the user is outside a predefined location range. Similarly, the height of the blood pressure sensor may be determined to be at the heart level of the user where the determined angle of the device with respect to the direction of gravity is within a predefined angle range, the identified location of the one or more features of the user is within a predefined location range, or both the determined angle of the device with respect to the direction of gravity is within a predefined angle range and the identified location of the one or more features of the user is within a predefined location range.

Thus, in some embodiments, both of the described parameters (namely, the parameters of the determined angle of the device 100 with respect to the direction of gravity and the identified location of the one or more anatomical features of the user in the image relative) may be checked. If one or both of these parameters are outside their respective predefined ranges, the height of the blood pressure sensor 102 may be determined to be different to the heart level of the user (which may, for example, be a height that is inappropriate or less than optimal for blood pressure measurements). On the other hand, if one or both of these parameters are within their respective predefined ranges, the height of the blood pressure sensor 102 may be determined to be at the heart level of the user (which may, for example, be a height that is appropriate or optimal for blood pressure measurements).

In embodiments in which the distance of the device 100 with respect to the body is determined based on the location of the one or more features, the determination of the height of the blood pressure sensor 102 relative to the heart level of the user may be further based on this determined distance. In this way, the height of the blood pressure sensor 102 relative to the heart level may be determined more precisely, or an absolute deviation of the height of the blood pressure sensor 102 from the heart level (for example, in centimetres) may be determined.

Figure 3:
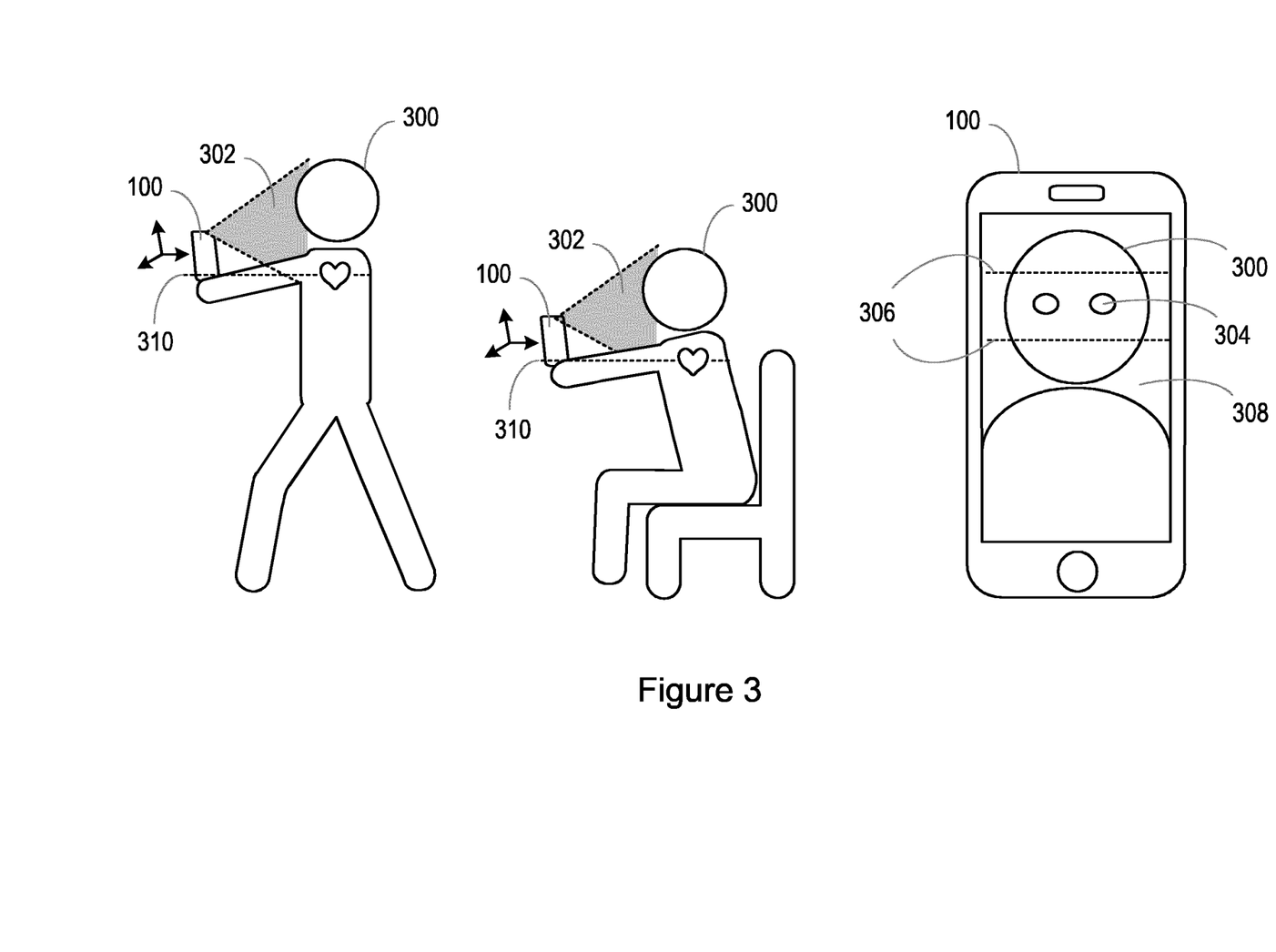
FIG. 3 is an illustration of a device in use according to an embodiment.

FIG. 3 is an illustration of the device 100 in use by a user 300 according to an embodiment. As illustrated in FIG. 3, an angular sensor is used to determine the angle that the device 100 makes relative to the direction of gravity and a camera is used to identify the location of one or more features of the user 300 when the user 300 is (at least partially) in the field of view 302 of the camera.

In this illustrated example embodiment, an image of the user and a predefined location range 306 is displayed on a display 308 of the device 100 comprising the blood pressure sensor 102. However, as described earlier, the image of the user and the predefined location range 306 may instead be displayed on a display of a device 100 that is a different device to the device 100 comprising the blood pressure sensor 102 according to other example embodiments. The predefined location range 306 defines a location range on the display 308 of the device 100 for the user to align one or more of their features (such as any of those mentioned earlier). In the example embodiment shown in FIG. 3, the one or more features of the user are the eyes 304 of the user. Thus, in the example embodiment shown in FIG. 3, the location of the eyes 304 of the user relative to the predefined location range 306 of the display 308 of the device 100 are identified (at block 204 of FIG. 2). As described above, a height of the blood pressure sensor of the device 100 relative to a heart level 310 of the user 300 can be determined (at block 206 of FIG. 2) based on the determined angle of the device 100 with respect to the direction of gravity and the identified location of the one or more features of the user 300.

Through the determined height of the blood pressure sensor 102 relative to the heart level of the user, the combination of the determined angle of the device 100 with respect to the direction of gravity and the identified location of one or more features of the user holding the device 100 (or the combination of an angular sensor and a camera) can be used to control the device 100 to ensure that hydrostatic effects are minimised or eliminated. Thus, returning back to FIG. 2, at block 208, the device 100 is controlled based on the determined height of the blood pressure sensor 102 relative to the heart level of the user. The device 100 can be controlled based on the determined height of the blood pressure sensor 102 relative to the heart level of the user in a variety of ways.

In some embodiments, when the height of the blood pressure sensor is determined to be at the heart level of the user, the blood pressure sensor 102 of the device 100 may be controlled to acquire a blood pressure measurement from the user.

In some embodiments, when the height of the blood pressure sensor 102 is determined to be different to the heart level of the user, the device 100 may be controlled to output to the user one or more of the determined angle of the device 100 with respect to the direction of gravity and the identified location of the one or more features of the user (such as via a user interface 110, which can be a user interface of the device or a user interface external to the device). In some embodiments, the predefined angle range, the predefined location range, or both the predefined angle range and the predefined location range may also be output to the user (such as via a user interface 110, which can be a user interface of the device or a user interface external to the device). In this way, information is provided that enables the user to ensure that the device 100 is positioned to avoid hydrostatic effects such that an accurate blood pressure measurement can be acquired from the blood pressure sensor 102.

Alternatively or in addition, in some embodiments, when the height of the blood pressure sensor 102 is determined to be different to the heart level of the user, the device 100 may be controlled to output to the user an instruction to adjust any one or more of the angle of the device 100 with respect to the direction of gravity, the location (for example, the height) of the one or more features of the user, and the angle of the body (or posture) of the user. As mentioned earlier, the angle of the body of the user may be inferred from the angle of the device 100 with respect to the direction of gravity. The device 100 may be controlled to output the instruction to the user via a user interface 110, which can be a user interface of the device or a user interface external to the device.

The instruction may be, for example, an instruction to move the device 100 in a certain direction, an instruction to tilt the device 100 in a certain direction, an instruction to alter the angle of the body (or posture) of the user, or any combination of these instructions. In some embodiments, an instruction may be output whenever the height of the blood pressure sensor 102 is determined to be different to the heart level of the user. For example, in some embodiments, an instruction may be output whenever the determined angle of the device 100 with respect to the direction of gravity is outside the predefined angle range, the identified location of the one or more features of the user is outside the predefined location range, or both the determined angle of the device 100 with respect to the direction of gravity is outside the predefined angle range and the identified location of the one or more features of the user is outside the predefined location range. In this way, feedback can be provided to the user to guide the user to position the device 100 at (or near or closer to) the heart level of the user at the appropriate orientation to reduce or eliminate hydrostatic effects.

Alternatively or in addition, in some embodiments, when the height of the blood pressure sensor is determined to be different to the heart level of the user, the device 100 may be controlled to output to the user an error notification (such as via a user interface 110, which can be a user interface of the device or a user interface external to the device). The error notification may, for example, indicate that a blood pressure measurement is false, incorrect, or has not been determined.

In some embodiments, an error notification may be output whenever the height of the blood pressure sensor 102 is determined to be different to the heart level of the user. For example, in some embodiments, an error notification may be output whenever the determined angle of the device 100 with respect to the direction of gravity is outside the predefined angle range, the identified location of the one or more features of the user is outside the predefined location range, or both the determined angle of the device 200 with respect to the direction of gravity is outside the predefined angle range and the identified location of the one or more features of the user is outside the predefined location range. In this way, the user can be guided to position the device 100 differently until the device 100 is at (or near) the heart level of the user at the appropriate orientation to reduce or eliminate hydrostatic effects.

In some embodiments, the error notification may be output where the angle of the device 100 with respect to the direction of gravity is more than a predefined threshold value. For example, the predefined threshold value may be at or around 90 degrees to prevent blood pressure measurements being acquired when the user is laying down (since, as mentioned earlier, the angle of the body of the user may be inferred from the angle of the device 100 with respect to the direction of gravity).

Alternatively or in addition, in some embodiments, when the height of the blood pressure sensor 102 is determined to be different to the heart level of the user, the blood pressure sensor 102 of the device 100 may be controlled to acquire a blood pressure measurement from the user. In these embodiments, the acquired blood pressure measurement can then be adjusted based on the difference between the height of the blood pressure sensor and the heart level of the user.

The difference between the height of the blood pressure sensor and the heart level of the user can be determined as an absolute height difference. In some embodiments, for example, the difference between the height of the blood pressure sensor and the heart level of the user may be determined based on the location of the one or more features of the user holding the device in relation to a target location for the one or more features of the user for the blood pressure sensor 102 of the device 100 to be positioned at the heart level of the user. The height difference may be determined as the number of pixels between the identified location of the one or more features of the user holding the device and the target location for the one or more features. In some embodiments, a scaling factor may be used to relate the number of pixels to a distance measurement (for example, centimetres) for the height difference. For example, where a feature of the user is located six pixels below the target location for that feature, the height difference may be determined as six pixels times the scaling factor.

In embodiments where the distance of the device 100 with respect to the body is determined based on the location of the one or more features, the determined distance may also be used in the determination of the height difference. For example, the scaling factor can be made dependent on the determined distance of the device 100 with respect to the body.

The error that is made in a blood pressure measurement with hydrostatic effects is based on the difference between the height of the blood pressure sensor and the heart level of the user. Thus, adjustment of the acquired blood pressure measurement can comprise determining the hydrostatic offset from the determined difference between the height of the blood pressure sensor and the heart level of the user. Then, the determined hydrostatic offset can be used to remove hydrostatic effects from the acquired blood pressure measurement. For example, where the determined difference between the height of the blood pressure sensor and the heart level of the user indicates that the blood pressure sensor is above the heart level over the user, the determined hydrostatic effect is removed from the acquired blood pressure measurement by adding the hydrostatic offset to the acquired blood pressure measurement. Similarly, where the determined difference between the height of the blood pressure sensor and the heart level of the user indicates that the blood pressure sensor is below the heart level over the user, the determined hydrostatic effect is removed from the acquired blood pressure measurement by subtracting the hydrostatic offset to the acquired blood pressure measurement.

The hydrostatic offset in an acquired blood pressure measurement is approximately 0.75 mmHg per cm of height difference between the height of the blood pressure sensor and the heart level of the user. Thus, for example, where the blood pressure sensor 102 is determined to be 10 cm above the heart level of the user, the acquired blood pressure measurement can be adjusted by adding 10*0.75=7.5 mmHg to the acquired blood pressure measurement. In this way, any hydrostatic effects that would otherwise distort the acquired blood pressure measurement can be compensated (or corrected) to thus provide a more accurate blood pressure measurement.

In any of the embodiments where the blood pressure sensor 102 of the device 100 is controlled to acquire a blood pressure measurement from the user, the blood pressure measurement may be acquired from the user using any suitable technique for acquiring a blood pressure measurement. As mentioned earlier, the blood pressure measurement may be acquired from arterial oscillations detected by the blood pressure sensor 102. The arterial oscillations can comprise volumetric oscillations, pressure oscillations, or both volumetric and pressure oscillations. The arterial oscillations can be detected as a function of applied pressure. In these embodiments, the arterial oscillations versus applied pressure can be processed using standard techniques to acquire the blood pressure measurement (such as any one or more of a value for the systolic blood pressure, the diastolic blood pressure, and mean arterial blood pressure).

In any of the embodiments in which a blood pressure measurement is acquired, the method may further comprise providing (for example, rendering, outputting, or displaying) the acquired blood pressure measurement to the user. For example, as mentioned earlier, the control unit 104 may control a user interface 110 (which may be a user interface of the apparatus 100 or a user interface external to the device) to provide (for example, render, output, or display) to the user the acquired blood pressure measurement.

There is therefore provided an improved device comprising a blood pressure sensor and an improved method for controlling the device. As described herein, the device can be controlled in a manner that can help to reduce, prevent, or eliminate hydrostatic effects in blood pressure measurements. In this way, more accurate blood pressure measurements can be acquired by way of a simple yet effective method.

There is also provided a computer program product comprising a computer readable medium, the computer readable medium having computer readable code embodied therein. The computer readable code is configured such that, on execution by a suitable computer or processor, the computer or processor is caused to perform the method or methods described herein.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for controlling a device comprising a blood pressure sensor comprising:
    determining an angle of the device with respect to the direction of gravity;
    identifying, in an image of a user, a location of one or more anatomical features of the user holding the device;
    determining whether the determined angle is within a range of predefined angles;
    determining whether the determined location is within a range of predefined locations in the image;
    determining whether the blood pressure sensor is at a heart level of the user based on the determined angle and the determined location;
    wherein the blood pressure sensor is determined to be at the heart level whenever the determined angle is within the range of predefined angles and the identified location is within the range of predefined locations; and
    controlling the blood pressure sensor to acquire a blood pressure measurement from the user when the blood pressure sensor is determined to be at the heart level of the user.

2. The method as claimed in claim 1, wherein controlling the device comprises:
    controlling the device to output to the user the determined angle of the device with respect to the direction of gravity and the identified location of the one or more anatomical features of the user when the blood pressure sensor is determined not to be at the heart level of the user.

3. The method as claimed in claim 1, wherein controlling the device comprises:
    controlling the device to output to the user an instruction to adjust the angle of the device with respect to the direction of gravity and the location of the one or more anatomical features of the user when the blood pressure sensor is determined not to be at the heart level of the user.

4. The method as claimed in claim 1, wherein controlling the device comprises:
    controlling the device to output to the user an error notification when the blood pressure sensor is determined not to be at the heart level of the user.

5. The method as claimed in claim 1, wherein controlling the device comprises:
    determining a height of the blood pressure sensor relative to the heart level of the user based on the identified location of the one or more anatomic features in the image;
    controlling the blood pressure sensor to acquire a blood pressure measurement from the user when the height of the blood pressure sensor is determined to be different to the heart level of the user; and
    adjusting the acquired blood pressure measurement based on the difference between the height of the blood pressure sensor and the heart level of the user.

6. The method as claimed in claim 1, wherein the one or more anatomical features of the user comprise at least one of:
    one or both eyes of the user;
    the mouth of the user; and
    the nose of the user.

7. A non-transitory computer-readable medium that includes a program that, when executed by a processor, causes the processor to control a device comprising a blood pressure sensor by:
    determining an angle of the device with respect to the direction of gravity;
    identifying, in an image of the user, a location of one or more anatomical features of the user holding the device;
    determining whether the angle of the device is within a range of predefined angles;
    determining whether the location of the one or more anatomical features is within a range of predefined locations in the image;
    determining whether the blood pressure sensor is at a heart level of the user based on the determined angle and the determined location;
    wherein the blood pressure sensor is determined to be at a heart level of the user whenever the determined angle is within the range of predefined angles and the identified location is within the range of predefined locations; and controlling the blood pressure sensor to acquire a blood pressure measurement from the user when the blood pressure sensor is determined to be at the heart level of the user.

8. The medium as claimed in claim 7, wherein the program further causes the processor to:

determine a height of the blood pressure sensor relative to the heart level of the user based on the identified location of the one or more anatomic features in the image;

control the blood pressure sensor to acquire a blood pressure measurement from the user when the height of the blood pressure sensor is determined to be different to the heart level of the user; and adjust the acquired blood pressure measurement based on the difference between the height of the blood pressure sensor and the heart level of the user.

9. The medium as claimed in claim 7, wherein the program further causes the processor to provide the blood pressure measurement to a display.

10. The medium as claimed in claim 7, wherein the program further causes the processor to output to the user an error notification when the height of the blood pressure sensor is determined not to be at the heart level of the user.

11. The medium as claimed in claim 7, wherein the one or more anatomical features of the user comprise at least one of:

one or both eyes of the user;
the mouth of the user; and
the nose of the user.

12. A device comprising:

a blood pressure sensor for acquiring a blood pressure measurement from a user holding the device; and a control unit configured to:

determine an angle of the device with respect to the direction of gravity;

identify, in an image of the user, a location of one or more anatomical features of the user holding the device;

determine whether the angle of the device is within a range of predefined angles;

determine whether the location of the one or more anatomical features is within a range of predefined locations in the image;

determine whether the blood pressure sensor is at a heart level of the user based on the determined angle and the determined location;

wherein the blood pressure sensor is determined to be at a heart level of the user whenever the determined angle is within the range of predefined angles and the identified location is within the range of predefined locations; and control the blood pressure sensor to acquire a blood pressure measurement from the user when the blood pressure sensor is determined to be at the heart level of the user.

13. The device as claimed in claim 12, the device further comprising:

an angular sensor, wherein the control unit is configured to control the angular sensor to determine the angle of the device with respect to the direction of gravity.

14. The device as claimed in claim 12, the device further comprising:

a camera, wherein the control unit is configured to control the camera to identify the range of predefined locations in a display of the image of the user.

15. The device as claimed in claim 12, the device further comprising:

a user interface, wherein when the blood pressure sensor is determined not to be at the heart level of the user, the control unit is configured to control the user interface to output to the user any one or more of:

the determined angle of the device with respect to the direction of gravity;

the identified location of the one or more anatomical features of the user;

an instruction to adjust at least one of:

the angle of the device with respect to the direction of gravity, the location of the one or more anatomical features of the user in the image of the user, and an angle of the body of the user; and an error notification.

16. The device as claimed in claim 12, wherein the blood pressure sensor comprises at least one of:

a volume sensor; and
a pressure sensor.

17. The device as claimed in claim 12, wherein the control unit is configured to:

determine a height of the blood pressure sensor relative to the heart level of the user based on the identified location of the one or more anatomic features in the image;

control the blood pressure sensor to acquire a blood pressure measurement from the user when the height of the blood pressure sensor is determined to be different to the heart level of the user; and adjust the acquired blood pressure measurement based on the difference between the height of the blood pressure sensor and the heart level of the user.

18. The device as claimed in claim 12, further comprising a display, wherein the control unit is configured to provide the blood pressure measurement to the display.

19. The device as claimed in claim 12, wherein the control unit is configured to output to the user an error notification when the height of the blood pressure sensor is determined not to be at the heart level of the user.

20. The device as claimed in claim 12, wherein the one or more anatomical features of the user comprise at least one of:

one or both eyes of the user;
the mouth of the user; and
the nose of the user.

* * * * *